US009247788B2

(12) United States Patent
Brace et al.

(10) Patent No.: US 9,247,788 B2
(45) Date of Patent: Feb. 2, 2016

(54) PERSONAL PROTECTIVE EQUIPMENT STRAP RETAINING DEVICES

(71) Applicant: 3M INNOVATIVE PROPERTIES COMPANY, St. Paul, MN (US)

(72) Inventors: Thomas J. Brace, St. Paul, MN (US); William A. Mittelstadt, Woodbury, MN (US); David M. Blomberg, Lino Lakes, MN (US)

(73) Assignee: 3M Innovative Properties Company, St. Paul, MN (US)

(*) Notice: Subject to any disclaimer, the term of this patent is extended or adjusted under 35 U.S.C. 154(b) by 87 days.

(21) Appl. No.: 13/833,309

(22) Filed: Mar. 15, 2013

(65) Prior Publication Data

US 2014/0216476 A1 Aug. 7, 2014

Related U.S. Application Data

(63) Continuation-in-part of application No. 13/756,895, filed on Feb. 1, 2013.

(51) Int. Cl.

| | |
|---|---|
| ***A61B 19/00*** | (2006.01) |
| ***A44B 11/25*** | (2006.01) |
| ***A62B 18/08*** | (2006.01) |
| *A41D 13/11* | (2006.01) |
| *A44B 11/06* | (2006.01) |

(52) U.S. Cl.

CPC ........... *A44B 11/2592* (2013.01); *A62B 18/084* (2013.01); *A41D 13/1161* (2013.01); *A44B 11/06* (2013.01); *Y10T 24/45581* (2015.01)

(58) Field of Classification Search

CPC ........... A41D 13/1161; A44B 11/2592; A44B 11/06; A44B 11/065; A61F 9/025; A61F 9/027; G02C 1/04; G02C 2200/06; G02C 2200/08; G02C 3/003; G02C 5/2263; A62B 18/084; Y10T 24/45581; Y10T 24/214

USPC ........... 128/858, 863, 201.19, 873; 24/16 PB, 24/634, 635

See application file for complete search history.

(56) References Cited

U.S. PATENT DOCUMENTS 2,928,387 A * 3/1960 Layne ...................... 128/201.19
2,998,818 A 9/1961 Tabor
3,013,556 A 12/1961 Galleher, Jr.

(Continued)

FOREIGN PATENT DOCUMENTS

CA 2 402 743 10/2001
CN 2800855 6/2005

(Continued)

OTHER PUBLICATIONS

International Application PCT/US2014/011587 Search Report dated Nov. 26, 2014.

*Primary Examiner* — Michael Brown
(74) *Attorney, Agent, or Firm* — Peter L. Olson

(57) ABSTRACT

A strap retaining device having an actuation arm that may engage a retaining tab is provided. In an exemplary embodiment, the strap retaining device includes a frame, a retention tab pivotally connected to the frame, and an actuation arm connected to the frame and having a first actuation element movable towards the retention tab from a neutral position to an actuated. The first actuation ramp is movable in a first plane to cause the retention tab to move in a second plane that is perpendicular to the first plane.

26 Claims, 6 Drawing Sheets

(56) References Cited

U.S. PATENT DOCUMENTS

| | | | | | |
|---|---|---|---|---|---|
| 3,154,073 | A | | 10/1964 | Klinger | |
| 3,605,204 | A | | 9/1971 | Amundsen | |
| 3,900,923 | A | * | 8/1975 | Thomas | 24/16 PB |
| 4,062,357 | A | | 12/1977 | Laerdal | |
| 4,419,993 | A | | 12/1983 | Petersen | |
| 4,536,440 | A | | 8/1985 | Berg | |
| 4,727,630 | A | * | 3/1988 | Alan | 24/593.11 |
| 4,790,306 | A | | 12/1988 | Braun | |
| 4,807,619 | A | | 2/1989 | Dyrud | |
| 4,843,688 | A | | 7/1989 | Ikeda | |
| 4,850,347 | A | | 7/1989 | Skov | |
| 4,874,399 | A | | 10/1989 | Reed | |
| 4,971,052 | A | | 11/1990 | Edwards | |
| 5,025,052 | A | | 6/1991 | Crater | |
| 5,035,239 | A | | 7/1991 | Edwards | |
| 5,062,421 | A | | 11/1991 | Burns | |
| 5,099,026 | A | | 3/1992 | Crater | |
| 5,181,280 | A | | 1/1993 | Zachry | |
| 5,181,507 | A | | 1/1993 | Michel et al. | |
| 5,307,796 | A | | 5/1994 | Kronzer | |
| 5,411,576 | A | | 5/1995 | Jones | |
| 5,441,046 | A | | 8/1995 | Starr | |
| 5,472,481 | A | | 12/1995 | Jones | |
| 5,558,089 | A | | 9/1996 | Castiglione | |
| 5,566,427 | A | | 10/1996 | Lathrop | |
| 5,617,849 | A | | 4/1997 | Springett | |
| 5,657,493 | A | | 8/1997 | Ferrero | |
| 5,706,804 | A | | 1/1998 | Baumann | |
| 5,711,036 | A | | 1/1998 | Kita | |
| 5,724,677 | A | | 3/1998 | Bryant | |
| 5,727,259 | A | | 3/1998 | Kawamata | |
| 5,906,033 | A | | 5/1999 | Mukaiyama | |
| 5,908,598 | A | | 6/1999 | Rousseau | |
| 5,924,420 | A | | 7/1999 | Reischel | |
| D424,688 | S | | 5/2000 | Bryant | |
| 6,057,256 | A | | 5/2000 | Krueger | |
| 6,062,221 | A | | 5/2000 | Brostrom | |
| 6,068,799 | A | | 5/2000 | Rousseau | |
| 6,119,692 | A | | 9/2000 | Byram | |
| 6,123,077 | A | | 9/2000 | Bostock | |
| D431,647 | S | | 10/2000 | Henderson | |
| 6,125,849 | A | | 10/2000 | Williams | |
| 6,161,267 | A | * | 12/2000 | Trautwein | 24/635 |
| 6,213,122 | B1 | | 4/2001 | Rousseau | |
| 6,238,466 | B1 | | 5/2001 | Rousseau | |
| D443,927 | S | | 6/2001 | Chen | |
| 6,432,175 | B1 | | 8/2002 | Jones | |
| 6,457,473 | B1 | | 10/2002 | Brostrom | |
| 6,691,378 | B1 | | 2/2004 | Chou | |
| 6,694,532 | B2 | | 2/2004 | Chen | |
| 6,732,733 | B1 | | 5/2004 | Brostrom | |
| 6,928,657 | B2 | | 8/2005 | Bell | |
| 7,028,689 | B2 | | 4/2006 | Martin | |
| 7,275,536 | B2 | | 10/2007 | Godoy | |
| 7,296,305 | B2 | | 11/2007 | Ketterer | |
| 7,340,804 | B2 | | 3/2008 | Saderholm | |
| 8,132,603 | B2 | | 3/2012 | Hogan | |
| 2003/0084903 | A1 | | 5/2003 | Fecteau | |
| 2003/0154984 | A1 | | 8/2003 | Fernandes | |
| 2004/0035428 | A1 | | 2/2004 | Olsen | |
| 2006/0207600 | A1 | | 9/2006 | Burrow | |
| 2009/0300888 | A1 | | 12/2009 | Shiue | |
| 2012/0222202 | A1 | | 9/2012 | Chang | |
| 2012/0266418 | A1 | | 10/2012 | Chou | |
| 2014/0216472 | A1 | | 8/2014 | Brace | |

FOREIGN PATENT DOCUMENTS

| | | |
|---|---|---|
| DE | 9300181 | 1/1993 |
| DE | 9419623 | 3/1995 |
| DE | 29517776 | 3/1996 |
| EP | 1 001 830 | 3/2004 |
| EP | 1454825 | 9/2004 |
| EP | 1495785 | 1/2005 |
| GB | 523822 | 1/1939 |
| GB | 2059782 | 4/1981 |
| GB | 2092009 | 8/1982 |
| GB | 2 338 787 | 11/2003 |
| GB | 2429537 | 2/2007 |
| GB | 2 454 451 | 5/2009 |
| GB | 2 477 738 | 8/2011 |
| GB | 2 489 045 | 3/2013 |
| JP | 53-153700 | 12/1978 |
| JP | 2010864 | 1/1990 |
| JP | 07-185027 | 7/1995 |
| JP | 10-99457 | 4/1998 |
| JP | 10-201866 | 8/1998 |
| JP | 2000-140139 | 5/2000 |
| JP | 2000-288107 | 10/2000 |
| JP | 2001-104501 | 4/2001 |
| JP | 2004-267694 | 9/2004 |
| JP | 2005-000218 | 1/2005 |
| JP | 2005-103045 | 4/2005 |
| JP | 2005-124818 | 5/2005 |
| JP | 2005-143860 | 6/2005 |
| JP | 2005-152229 | 6/2005 |
| JP | 3117487 | 11/2005 |
| KR | 2000-014559 | 7/2000 |
| KR | 20-0241398 | 7/2001 |
| KR | 2001-0090697 | 10/2001 |
| KR | 10-0374386 | 2/2003 |
| KR | 20-0313897 | 5/2003 |
| KR | 10-0396183 | 8/2003 |
| KR | 20-0338209 | 12/2003 |
| KR | 20-2003-036743 | 1/2004 |
| KR | 20-0352578 | 5/2004 |
| KR | 20-0384194 | 5/2005 |
| WO | 86/01734 | 3/1986 |
| WO | WO 86/01734 | 3/1986 |
| WO | WO 99/06116 | 2/1999 |
| WO | WO 99/17840 | 4/1999 |
| WO | WO 00/01737 | 1/2000 |
| WO | WO 00/50122 | 8/2000 |
| WO | WO 01/66194 | 9/2001 |
| WO | WO 2004/039185 | 5/2004 |
| WO | 2008/010193 | 1/2008 |
| WO | WO 2012/100116 | 7/2012 |

* cited by examiner

PERSONAL PROTECTIVE EQUIPMENT STRAP RETAINING DEVICES

TECHNICAL FIELD

This disclosure relates to strap retaining devices, in particular strap retaining devices for personal protective equipment having an actuation arm that may engage a retaining tab.

BACKGROUND

Personal protective devices often include one or more straps to secure the device in an appropriate position about a user. Respiratory protection devices that cover a user's nose and mouth, for example, often include one or more straps extending around the head of the user. In order to maintain a desired fit, straps may be elastic or adjustable to a suitable length for a particular user. Various strap retention devices and buckles have been provided that may allow for the length or tension of the strap to be manually adjusted.

SUMMARY

The present disclosure provides a strap retaining device for a personal protection device including a frame, a retention tab pivotally connected to the frame, and a first actuation arm connected to the frame and comprising a first actuation element movable towards the retention tab. The first actuation element is movable in a first plane from a neutral position to an actuated position in which the first actuation element causes the retention tab to move in a second plane that is substantially perpendicular to the first plane. In an exemplary embodiment, the first actuation element is a ramp, and the first actuation element contacts an angled surface of the retention tab in the actuated position. In various exemplary embodiments, the frame, strap retention tab, and actuation arm are integrally formed.

The present disclosure further provides a harness assembly for a respirator including first and second strap retaining devices each including a frame, a retention tab pivotally connected to the frame, a strap channel and a first actuation arm connected to the frame and comprising a first actuation ramp movable in a first plane from a neutral position to an actuated position in which the first actuation ramp contacts a surface of the retention tab and causes the retention tab to move in a second plane that is perpendicular to the first plane, a first strap positioned in a strap channel of the first strap retainer about a portion of the frame of the first strap retainer, and a second strap positioned in a strap channel of the second strap retainer about a portion of the frame of the second strap retaining devices. The first strap retaining device comprises a first attachment element and the second strap retaining device comprises a second attachment element and the first attachment element is attachable to the second attachment element.

The above summary is not intended to describe each disclosed embodiment or every implementation. The Figures and the Detailed Description, which follow, more particularly exemplify illustrative embodiments.

BRIEF DESCRIPTION OF DRAWINGS

The disclosure may be further explained with reference to the appended Figures, wherein like structure is referred to by like numerals throughout the several views, and wherein.

While the above-identified figures set forth various embodiments of the disclosed subject matter, other embodiments are also contemplated. In all cases, this disclosure presents the disclosed subject matter by way of representation and not limitation. It should be understood that numerous other modifications and embodiments can be devised by those skilled in the art which fall within the scope and spirit of the principles of this disclosure.

DETAILED DESCRIPTION

The present disclosure provides a personal protective equipment strap retaining device. The strap retaining device includes a retaining tab and one or more actuation arms. The retaining tab applies a force to a strap to limit the ability of the strap to slide through the strap retaining device. The one or more actuation tabs may be flexed to raise the retaining tab and allow the strap to slide through the retaining device more freely. An exemplary strap retaining device according to the present disclosure securely maintains the strap at a desired position, but allows a user to quickly and easily adjust the length of the strap by operating the one or more actuation arms.

Figure 1:
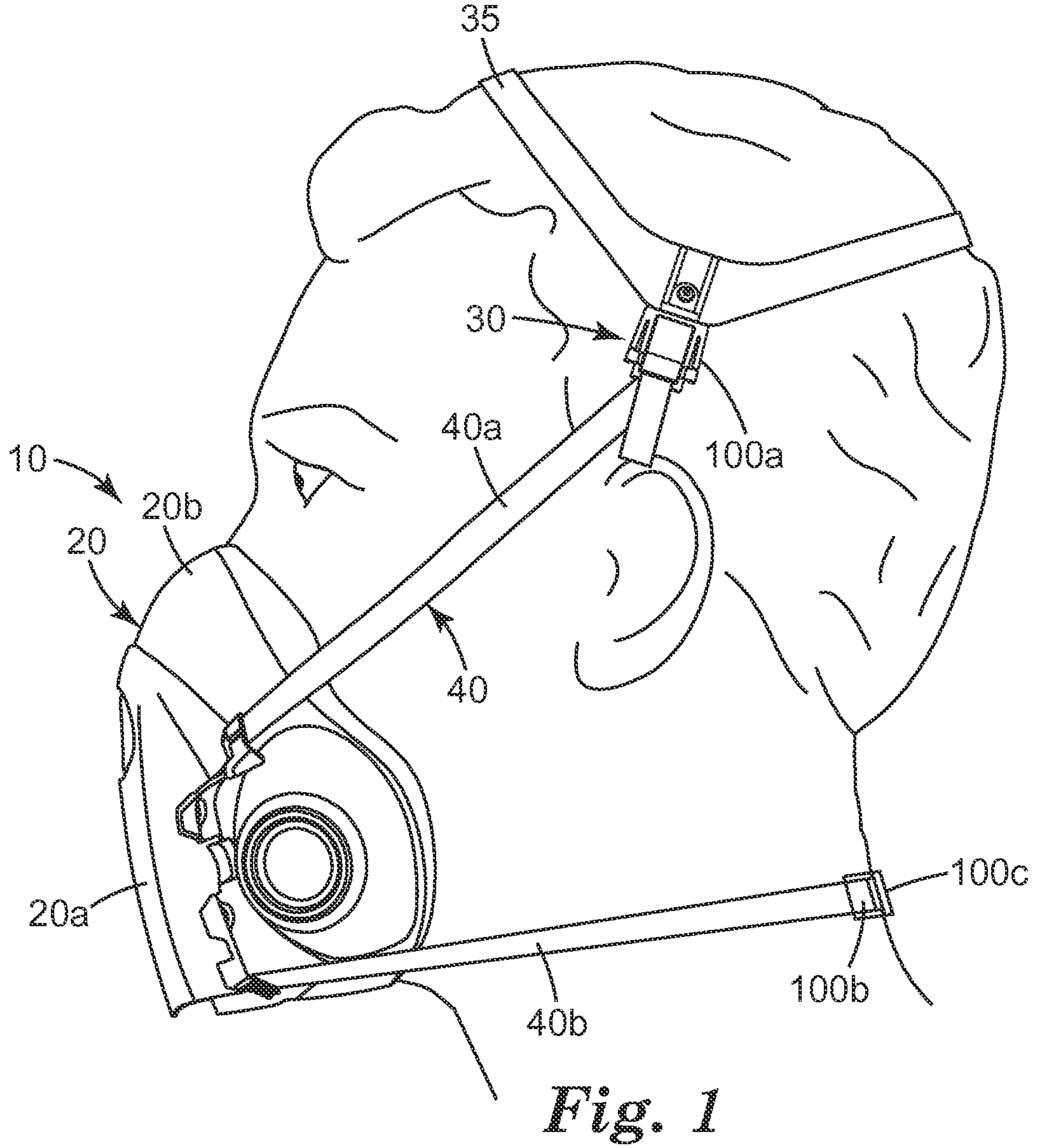
FIG. 1 shows a side view of an exemplary personal protective device including strap retaining devices according to the present disclosure.

FIG. 1 shows an exemplary personal protective device 10 including exemplary strap retaining devices 100*a*, 100*b*, 100*c*. The personal protective device 10 is a respiratory protection device including a mask body 20 and a harness assembly 30. The mask body may include a rigid or semi-rigid portion 20*a* and a face contacting portion 20*b*. The face contacting portion 20*b* may be formed of a soft or compliant material that provides a comfortable fit and is able to seal against the face of a wearer to prevent ingress of external air. The head harness assembly may include one or more straps 40, such as upper straps 40*a* and lower straps 40*b*, to secure respiratory protection device 10 in a position of use over the nose and mouth of the wearer. Upper straps 40*a* and lower straps 40*b* may be portions of a single continuous integral strap that passes through a loop or attachment element of mask body 20 or may be discrete individual straps that are each attached to mask body 20. In an exemplary embodiment, harness assembly 30 includes a strap support 35 configured to fit generally about the crown of a wearer's head. Strap support 35 may be made of any suitable material, and in some embodiments may be a head covering such as a cap, hard hat, hood, beanie, netting, or other suitable strap support. Upper and lower straps 40*a*, 40*b* may be appropriately tensioned such that face contacting portion 20*b* of mask body 20 is adequately positioned and/or sealed against a wearer's face.

In an exemplary embodiment, harness assembly 30 includes a first strap retaining device 100*a* attached to strap support 35 and allows for adjustment of upper strap 40*a*, for example. A second strap retaining device 100*b* is positioned proximate the rear of a wearer's neck and may allow adjustment of lower strap 40*b*, for example. In some exemplary embodiments, second strap retaining device is configured to be attached to a third retaining device 100*c* which allows for adjustment of another lower strap at an opposite side of the wearer's head. Strap retaining devices 100*a*, 100*b*, and/or 100*c* maintain a desired length of strap 40 between mask body 20 and strap support 35, for example, while allowing the desired length of strap 40 to be quickly and easily adjusted as described in greater detail below. U.S. application Ser. No. 13/757,337, titled Respiratory Protection Device Harness Assembly, addresses various embodiments of a harness assembly and attachment elements for a harness assembly, and is incorporated herein by reference.

Figure 2:
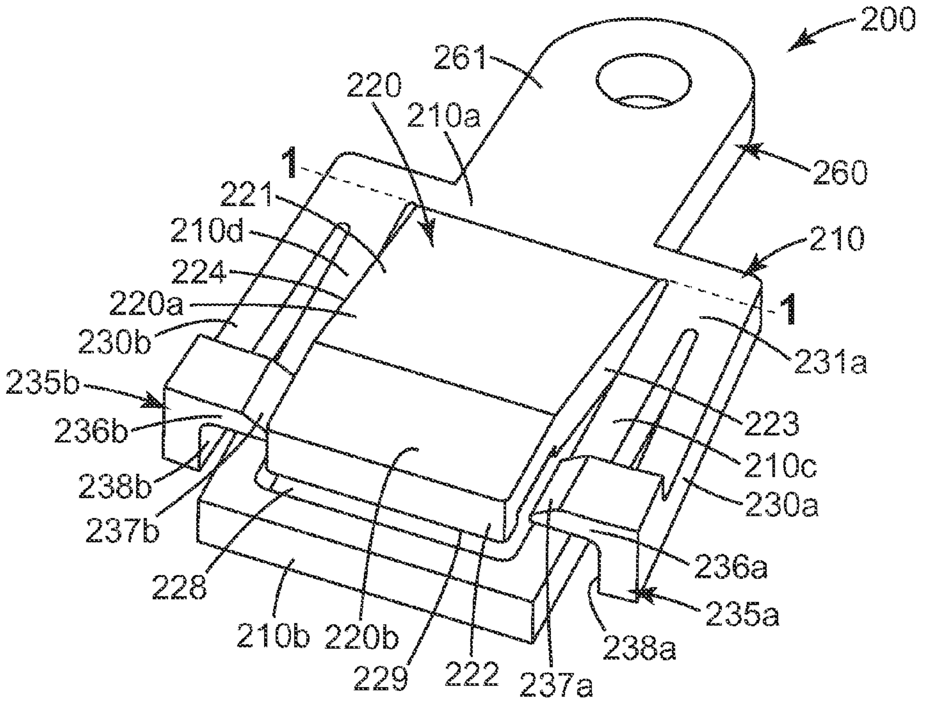
FIG. 2 shows a front perspective view of an exemplary strap retaining device according to the present disclosure.
Figure 3:
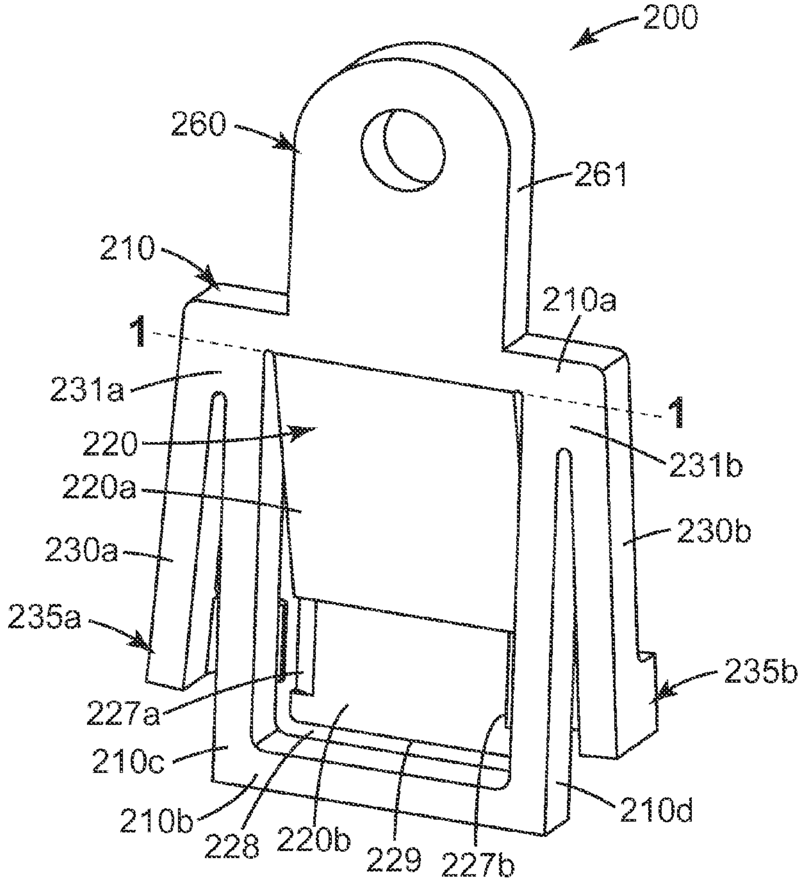
FIG. 3 shows a rear perspective view of an exemplary strap retaining device according to the present disclosure.

FIGS. 2 and 3 show an exemplary strap retaining device 200 according to the present disclosure. Strap retaining device 200 includes a frame 210, a retaining tab 220, and an actuation arm 230*a* attached to frame 210. Actuation arm 230*a* may engage retaining tab 220 to reduce a force applied by retaining tab 220 to a strap (not shown) positioned through strap retaining device 200.

In an exemplary embodiment, frame 210 provides a base that various portions of strap retaining device 200 may move relative to and may include a first frame portion 210*a*, and a second frame portion 210*b* in spaced relation to first frame portion 210*a*. First and second frame portions are connected by third and fourth frame portions 210*c* and 210*d*. First, second, third, and fourth frame portions 210*a*, 210*b*, 210*c*, 210*d* form a generally square or rectangular configuration and partially define a strap channel 228 for a strap to pass through, as described further below. Second frame portion 210*b* is positioned such that a strap may be looped around second frame portion 210*b*, and provides a base against which retaining tab 220 may clamp, or apply a force to, a strap to retain the strap at a desired length.

In the exemplary embodiment of FIG. 2, frame 210 includes four substantially straight frame portions with each frame portion joined to adjacent frame members at an angle of approximately 90 degrees. In other exemplary embodiments, frame 210 may comprise one, two, three, four, or more than four frame portions that exhibit an arcuate shape and may be joined to adjacent frame members at an angle other than 90 degrees. In an exemplary embodiment, frame 210 includes three frame portions, not including third frame portion 210*c*, for example, such that a strap may be more easily positioned in, or removed from, strap retaining device 200.

Retaining tab 220 extends from frame 210, for example from frame portion 210*a*. In an exemplary embodiment, retaining tab 220 includes first and second major surfaces separated by a thickness t, and may include an angled surface or ramped portion 220*a* extending away from frame portion 210*a* and generally upward from frame portion 210*a* and/or frame portions 210*b*, 210*c*, 210*d*. Retaining tab 220 may further include a clamp portion 220*b* including one or more retaining features 229. Retaining feature 229 may include a textured surface, sharp corner, serrated edge and/or other features that may provide additional friction or contact to retain a strap. In an exemplary embodiment, retaining tab 220 exhibits a cantilever configuration such that a first end portion 221 is connected to frame 210, first frame portion 210*a* for example, while first and second side portions 223, 224, and second end portion 222 are not connected to frame 210.

In an exemplary embodiment, retaining tab 220 is pivotally connected to frame portion 210*a* such that retaining tab 220 may pivot or rotate relative to an axis, such as axis 1-1, for example. In the embodiment of FIG. 2, axis 1-1 is proximate a connection between retaining tab 220 and first frame portion 210*a*. In other exemplary embodiments, retaining tab 220 may connect to one or more other portions of frame 210 such that the axis is proximate a central location of retaining tab 220 while two both first end portion 221 and second end portion 222 are not connected to frame 210 and are able to pivot or rotate.

Strap retaining device 200 includes one or more actuation arms that may be actuated to manipulate retaining tab 220. In an exemplary embodiment, strap retaining device 200 includes a first actuation arm 230*a* connected to frame 210, for example first or third frame portions 210*a* or 210*c*. First actuation arm 230*a* includes a first end portion 231*a* connected to frame 210, and extends as a cantilever from frame 210. Application of force along a length of arm 230*a*, such as a user squeezing arm 230*a* towards retaining tab 220, causes arm 230*a* to bend or flex about first end portion 231*a*. In an exemplary embodiment, a second actuation arm 230*b* is similarly connected to frame 210, for example first and fourth frame portions 210*a* or 210*d*, and generally mirrors first actuation arm 230*a*.

Arms 230*a*, 230*b* are biased towards a neutral or retained position, such as the position shown in FIG. 2, such that when an external force is removed, arm 230 returns to the neutral or retained position. In an exemplary embodiment, arm 230*a* returns to a fully neutral position when not squeezed or pressed by a user. In some exemplary embodiments, arm 230*a* may include a feature, such as a tab (not shown) that contacts a portion of frame 210, for example, that limits the return of arm 230*a* to a fully neutral position.

In an exemplary embodiment, first and second actuation arms 230*a*, 230*b* include actuation tabs 235*a*, 235*b* having extending portions 236*a*, 236*b* and actuation elements 237*a*, 237*b* that include actuation ramps configured to contact one or more surfaces of retaining tab 220 when arms 230*a*, 230*b* are flexed towards retaining tab 220. In various exemplary embodiments, actuation elements may be provide in the form of an edge, surface, chamfered corner, or any other suitable feature that may contact one or more surfaces of retaining tab 220 when arms 230*a*, 230*b* are flexed towards retaining tab 220.

Extending portions 236*a*, 236*b* position ramps 237*a*, 237*b* at desired positions relative to retaining tab 220. In an exemplary embodiment, extending portions 236*a*, 236*b* position ramps 237*a*, 237*b* proximate retaining tab 220 to allow ramps 237*a*, 237*b* to appropriately contact retaining tab 220 within a desired travel distance between a neutral position and a fully actuated position. A travel distance of ramps 237*a*, 237*b* may be limited by the distance between stop surfaces 238*a*, 238*b* and frame 210. In various exemplary embodiments, the distance between stop surfaces 238*a*, 238*b* and frame 210 when arms 230*a*, 230*b* are in a neutral or retained position is between approximately 10 mm and 1 mm, 6 mm and 1.5 mm, or of approximately 2 mm. Such a distance may allow easy actuation by a user while limiting the likelihood of inadvertent actuation. In the fully actuated position, a distance between stop surfaces 238*a*, 238*b* and frame 210 may be less than approximately 1 mm, or approximately 0 mm such that stop surfaces 238*a*, 238*b* contact frame 210 to limit further travel of arms 230*a*, 230*b* and ramps 237*a*, 237*b* when in a fully actuated position.

As shown in FIG. 3, for example, retaining tab may include engaging surfaces 227*a*, 227*b* having a shape complementary to ramps 237*a*, 237*b*. In an exemplary embodiment, engaging surfaces 227*a*, 227*b* are inward angled surfaces that allow retaining tab 220 to smoothly travel upward as actuation ramps 237*a*, 237*b* are moved from a neutral position to a fully actuated position. Other exemplary engaging surfaces included rounded or chamfered edges, or other suitable features.

Strap retaining device 200 may further include an attachment element 260. In an exemplary element, attachment element 260 extends from frame 210, such as frame member 210*a*, and extends away from frame 210 in a direction generally away from, and/or in an opposite direction of, retention tab 220. Attachment element 260 may include an anchoring tab 261, for example, shaped and configured for attachment. In an exemplary embodiment, anchoring tab 261 includes one or more recesses, cavities, projections, or other suitable features that may interact with complementary features of a harness assembly, such as a strap support, for example. Attachment element 260 thus may be releasably attached to the strap support, similar to the configuration of strap retaining device 100*a* shown in FIG. 1, for example. In some exemplary embodiments, attachment element 260 may be configured for attachment to other strap retaining devices. In this way, first and second straps or strap portions can be releasably attached by first and second strap retaining devices according to the present disclosure, similar to the configuration of strap retaining devices 100*b*, 100*c* shown in FIG. 1, for example.

Figure 4:
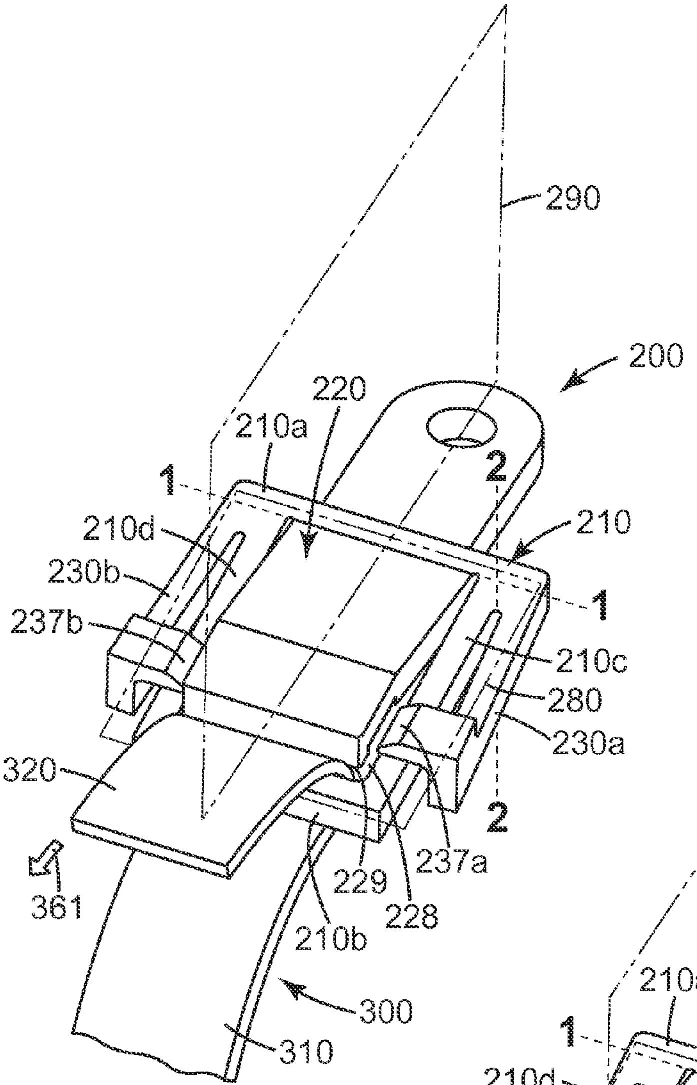
FIG. 4 shows a front perspective view of an exemplary strap retaining device and strap according to the present disclosure in a neutral or retained position.
Figure 5:
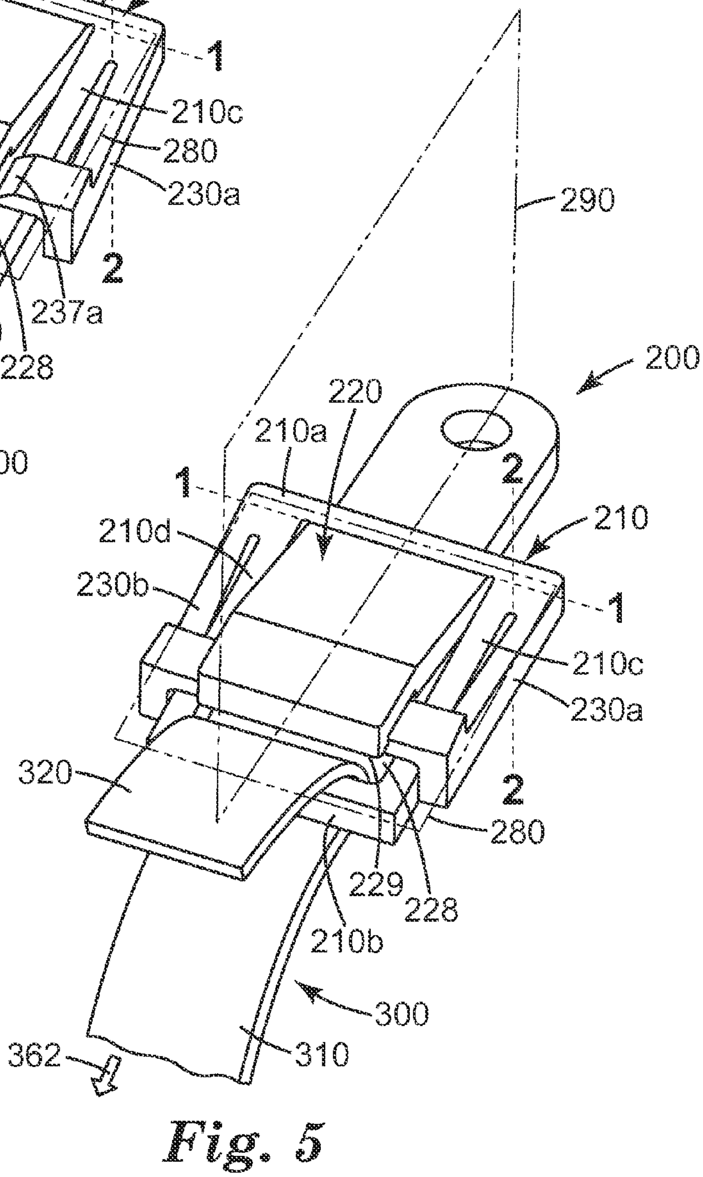
FIG. 5 shows a front perspective view of an exemplary strap retaining device and strap according to the present disclosure in an actuated position.

FIGS. 4 and 5 show an exemplary strap retaining device 200 and a strap 300 positioned through strap retaining device 200. Certain features of an exemplary strap retaining device 200 of the present disclosure may be understood in view of two reference planes defined relative to strap retaining device 200. A first plane 280 is generally parallel to a plane of rotation formed by actuator arms 230*a*, 230*b* as they move between neutral and actuated positions. That is, in an exemplary embodiment, actuator arms 230*a*, 230*b* move in first plane 280 when a force is applied to move actuator arms 230*a*, 230*b* from a neutral position to an actuated position. A second plane 290 divides strap retaining device 200 into imaginary first and second halves. First plane 280 and second plane 290 are substantially normal or perpendicular to each other. In various exemplary embodiments, first plane 280 and second plane 290 are substantially perpendicular such that first and second planes 280, 290 are within 5° of perpendicular, within 2° of perpendicular, or precisely perpendicular.

In an exemplary embodiment, retaining tab 220 may flex, pivot or rotate, for example, about an axis 1-1 that is generally parallel to first plane 280 and normal to second plane 290. Actuator arm 230*a*, for example, may flex, pivot or rotate, for example, about an axis 2-2 that is generally normal to first plane 280 and substantially parallel to second plane 290. Accordingly, actuator arm 230*a*, and actuation ramp 237*a* are moveable in first plane 280 towards retaining tab 220. When actuator arm 230*a* and actuation ramp 237*a* are moved from a neutral position, as shown in FIG. 4, to an actuated position, as shown in FIG. 5, actuation ramp 237*a* contacts engaging surface 227*a* of retaining tab 220 to move retaining tab 220 in the second plane. That is, in an exemplary embodiment, motion of arm 230*a* in first plane 280 results in movement of retaining tab 220 in second plane 290.

Strap 300 includes a tensioning portion 310 and a free end 320. Tensioning portion 310 may be attached to a personal protective device and maintains a personal protective device, such as a respiratory protection device, in an appropriate position. Free end 320 may provide excess length of strap if tension portion 310 is adjusted to a greater length, for example. In a neutral position shown in FIG. 4, retaining tab 220 and/or retaining features 229 contact strap 300 and may apply a force against strap 300 towards frame 210. A force applied to strap 300 may clamp strap 300 against frame 210 limiting movement of strap 300 through strap channel 228.

When a personal protective device including a strap retaining device 200 is positioned for use, a length of tensioning portion 310 can be decreased, and the strap tightened, by pulling free end 320 generally in a direction shown by arrow 361 for example. When free end 320 is pulled in direction 361, retaining tab 220 may bend, flex, or pivot, for example, and may lessen a force applied on strap 300 allowing the strap to pass through strap channel 228 and/or over frame portion 210*b*. When free end 320 is released, retaining tab 220 clamps strap 300 against frame 210 to retain strap 300 and maintain tension in tensioning portion 310. In an exemplary embodiment, although pulling free end 320 may allow strap 300 to move through strap channel 228 and shorten tensioning portion 310, pulling tension portion 310 does not result in strap 300 moving through strap channel 228 and lengthening tension portion 310. Additional tension may cause retaining tab 220 to be drawn closer to frame 210 increasing a force applied to strap 300 and further limiting movement of strap 300 through strap channel 228.

A length of tensioning portion 310 may be easily lengthened, and strap 300 loosened, by a user pushing actuating arms inwardly towards an actuated position shown in FIG. 5, for example. When a user squeezes actuation arms 230*a*, 230*b*, actuation ramps 237*a*, 237*b* contact engaging surfaces of retaining tab 220 causing retaining tab to move in second plane 290. Movement of retaining tab 220 increases a space between retaining tab and a portion of frame 210 such that strap 300 may more easily slide through strap channel 228. With actuation ramps 237*a*, 237*b* in an actuated position and retaining tab 220 raised, a user may easily increase a length of tensioning portion 310 of strap 300 to loosen the device about the user by pulling tension portion 310 in direction 362, for example.

The components and features of strap retaining device 200 may be formed separately and subsequently joined together to form strap retaining device 200. In an exemplary embodiment, frame 210, retaining tab 220, and one or more actuation arms 230 are formed integrally as a unitary piece, such as by injection molding. In other exemplary embodiments, one or more components may be separately formed and subsequently joined, using sonic welding or other suitable techniques, to form a unitary strap retaining device 200. A unitary construction provides a simple and relatively inexpensive strap retaining device that may be easily manufactured with few or no assembly or process steps required. Strap retaining device 200 is formed such that a unitary construction may be provided while allowing actuator arms 230*a*, 230*b* and retaining tab 220, respectively, to flex, pivot, or rotate in different planes that may be substantially perpendicular.

Retaining tab 220 and actuator arms 230*a*, 230*b*, and/or entire strap retaining device 200 may be formed from a material having suitable properties to allow for elastic deformation over a range of normal bending and flexing while exhibiting the ability of retaining tab 220 to apply an appropriate force to a strap positioned through strap retaining device 200. In an exemplary embodiment, retaining tab 220 and/or actuator arms 230_a_, 230_b_ are made from polypropylene such as a material having the trade name P5M4K-046 available from Flint Hills Resources of Wichita, Kans. Other suitable materials include plastics, polyethylene, acrylonitrile butadiene styrene (ABS), metals, spring steel, other suitable materials as known in the art, and suitable combinations of such materials.

The force required to move actuator arms to a fully actuated position may be dependant in part on the dimensions and geometry of actuator arms 230_a_, 230_b_ material properties of actuator arms 230_a_, 230_b_, and a force required to move retaining tab 220. The force required to move actuator arms 230_a_, 230_b_ for example, to an actuated position may be selected to be sufficiently low that actuator arms 230_a_, 230_b_ are easily moved to an actuated position by a user, but sufficiently high that inadvertent or unintentional actuation that could allow a strap to inadvertently loosen, for example, is unlikely to occur. In an exemplary embodiment, application of a total actuating force F of about 550 g results in actuation arms 230_a_, 230_b_ reaching fully actuated positions and moving retaining tab 220 in second plane 290. In the fully actuated position, a restoring force of about 550 g is likewise exerted by actuator arms 230_a_, 230_b_ to restore arms 230_a_, 230_b_ to a neutral position. In various exemplary embodiments, restoring force F is between about 50 g and 1000 g, or between about 250 g and 750 g.

In an exemplary embodiment, strap retaining device 200 provides a robust strap retaining device that may be used throughout the usable life of a personal protective device. In an exemplary embodiment, arms 230_a_, 230_b_ may move from neutral to actuated positions many times, in part because flexure of arms 230_a_, 230_b_ is desirably limited to an elastic regime. In various exemplary embodiments, a strap retaining device 200 provides arms 230_a_, 230_b_ that may be flexed between a neutral position and an actuated position 10,000 times, 100,000 times, or more than 100,000 times without fracture or damage that prevents strap retaining device 200 from functioning.

Figure 6:
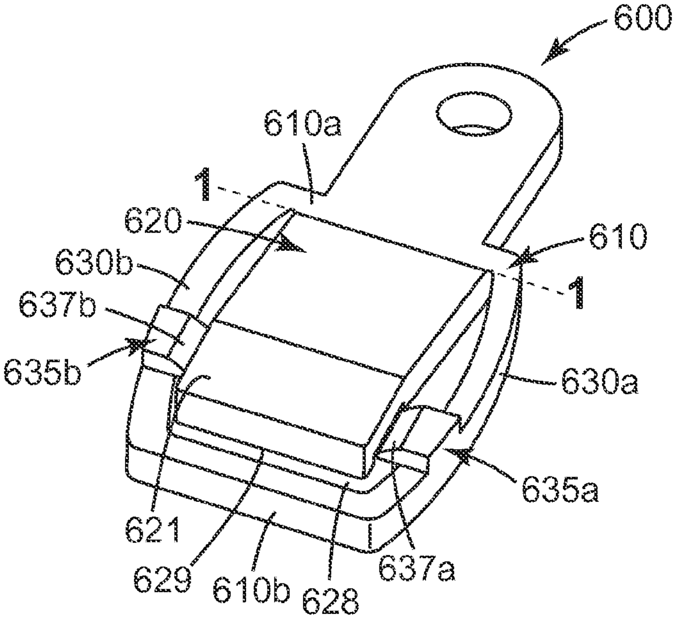
FIG. 6 shows a front perspective view of an exemplary strap retaining device according to the present disclosure in a retained position.
Figure 7:
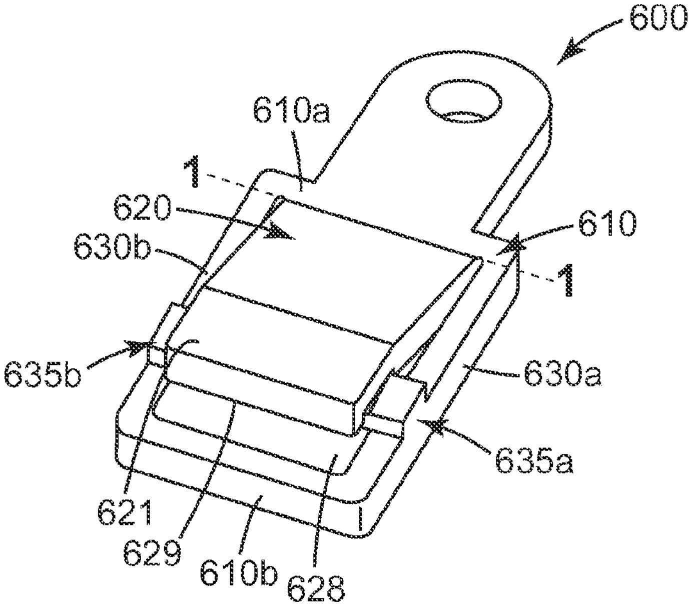
FIG. 7 shows a front perspective view of an exemplary strap retaining device according to the present disclosure in an actuated position.

FIGS. 6 and 7 show an exemplary embodiment of a strap retaining device 600 according to the present disclosure. Strap retaining device 600 includes frame 610, retaining tab 620, and one or more actuation arms, such as actuation arms 630_a_, 630_b_. Frame 610 includes a first frame portion 610_a_ and a second frame portion 610_b_ joined by first and second actuation arms 630_a_ and 630_b_. Actuation arms 630_a_, 630_b_ exhibit a curved configuration and generally curve outward between first and second frame portions 610_a_ and 610_b_.

Similar to strap retaining device 200 described above, retaining tab 620 is pivotally connected to frame portion 610_a_ such that retaining tab 620 may pivot or rotate relative to an axis, such as axis 1-1, for example. In a neutral position, retaining tab 620 and/or clamp portion 621, may apply a force against a strap positioned through strap channel 628.

In an exemplary embodiment, first and second actuation arms 630_a_, 630_b_ are connected to frame 610, extending between first and second frame portions 610_a_ and 610_b_, and having ends connected to frame portions 610_a_ and 610_b_, respectively. Application of force along a length of arms 630_a_, 630_b_, such as a user squeezing arms 630_a_, 630_b_ generally inwardly towards retaining tab 620, causes arms 630_a_, 630_b_ to flex and/or straighten. Arms 630_a_, 630_b_ are biased towards a curved neutral position, such as the position shown in FIG. 6, such that arms 630_a_, 630_b_ return to the curved neutral position when a force from a user is removed.

Actuation arms 630_a_, 630_b_ include actuation tabs 635_a_, 635_b_ having and actuation ramps 637_a_, 637_b_, respectively. Actuation ramps 637_a_, 637_b_ are configured to contact a surface of retaining tab 620 when arms 630_a_, 630_b_ are flexed and/or straightened towards retaining tab 620. In a neutral position shown in FIG. 6, retaining tab 620 and/or retaining features 629 contact a strap (not shown) and may apply a force against the strap towards frame 610. A force applied to the strap may clamp the strap against frame 610 limiting movement of the strap through strap channel 628. A length of the strap may be easily lengthened, and the strap loosened, by a user pushing actuating arms inwardly towards an actuated position shown in FIG. 7, for example. When a user squeezes actuation arms 630_a_, 630_b_, actuation arms 630_a_, 630_b_ flex and/or straighten causing actuation ramps 637_a_, 637_b_ to move in a first plane to contact engaging surfaces of retaining tab 620 and cause retaining tab 620 to move in a second plane. Movement of retaining tab 620 increases a space between retaining tab 620 and a portion of frame 610 such that the strap may more easily pass through strap channel 628. With actuation ramps 637_a_, 637_b_ in an actuated position and retaining tab 620 raised, a user may easily increase a length of the strap.

Figure 8:
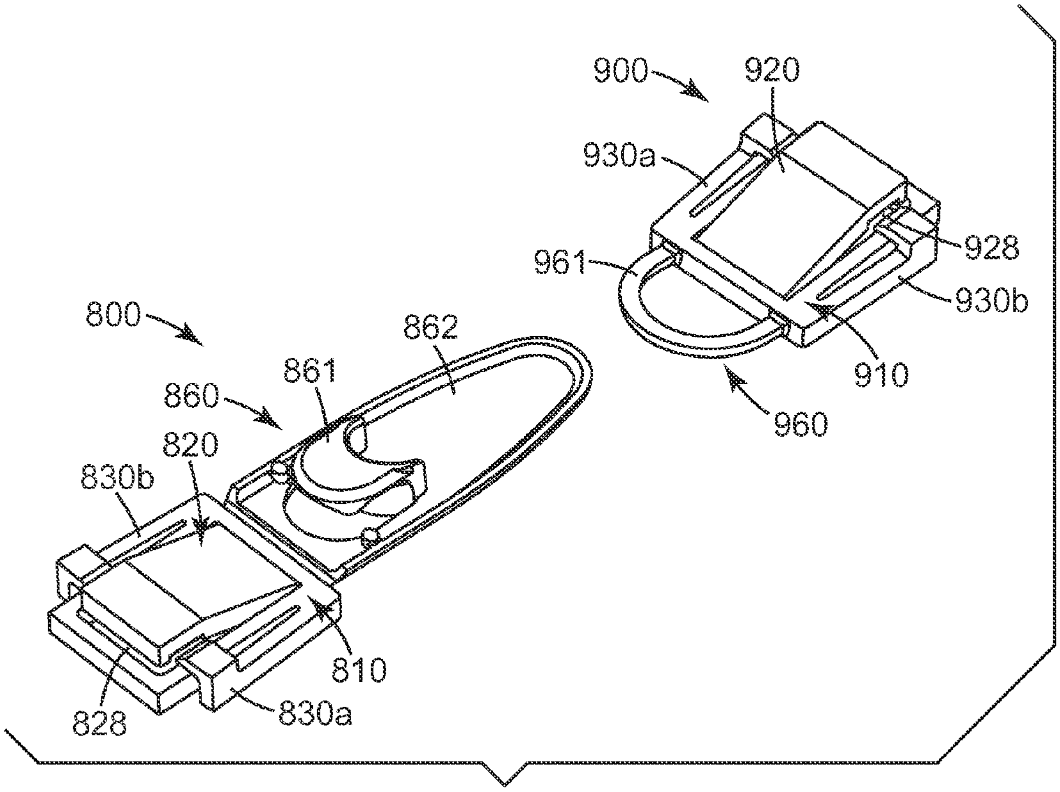
FIG. 8 shows a front perspective view of exemplary first and second strap retaining devices according to the present disclosure configured for attachment.

FIG. 8 shows exemplary embodiments of strap retaining devices 800 and 900 having attachment elements 860 and 960, respectively. Similar to strap retaining devices 200 and 600 described above, first and second strap retaining devices 800 and 900 include frames 810, 910, retention tabs 820, 920 pivotally connected to frames 810, 910, strap channels 828, 928 and first and second actuation arms 830_a_, 830_b_, 930_a_, 930_b_ connected to fames 810, 910, respectively. First and second actuation arms 830_a_, 830_b_, 930_a_, 930_b_ include actuation ramps movable towards retention tabs 820, 920 in a first plane to contact a surface of the retention tabs 820, 920 and move the retention tabs 820, 920 in a second plane that is substantially perpendicular to the first plane. First and second straps may be positioned in strap channels 828, 928.

First strap retainer 800 includes a first attachment element 860 that is attachable to a second attachment element 960 of second strap retainer 900. First and second attachment elements 860, 960 thus allow first and second straps or strap portions to be releasably attached, while also allowing easy tensioning or loosening of the first and second straps or strap portions, similar to the configuration of strap retaining devices 100_b_, 100_c_ of FIG. 1, for example. First and second attachment elements may include any suitable attachment feature that allows that first and second strap retaining devices to be attached. In an exemplary embodiment, first and second strap retaining devices 800, 900 are releasably attached, and are attached such that the straps are secure and not likely to be inadvertently separated but allowing for pivoting or relative rotation between first and second strap retaining devices 800, 900.

In an exemplary embodiment, first attachment element 860 comprises a hook 861 and second attachment element 960 comprises a loop 961. Loop 961 may be positioned within hook 861 to attach first and second attachment elements. When in use, tension of straps positioned in first and second strap retaining devices 800, 900 prevents separation of first and second attachment elements 860, 960. In an exemplary embodiment, first attachment element 860 further includes a generally planar member 862. When first and second attachment elements 860, 960 are attached, planar member 862 provides rigidity to the attachment such that second strap retaining device 900 is maintained in a desired orientation. In this way, pressure of strap retaining devices 800, 900 created by the tension of one or more straps is evenly distributed over a surface of a wearer's body that may be contacted by strap retaining devices 800, 900 such that no areas of focused pressure impinge on the wearer's body. First and second attachment elements 860, 960 may comprise other suitable attachment elements such as buckles, connectors, interference fits, hook and loop fasteners or other suitable features as known in the art that allow first and second strap retaining devices to be attachable.

Figure 9:
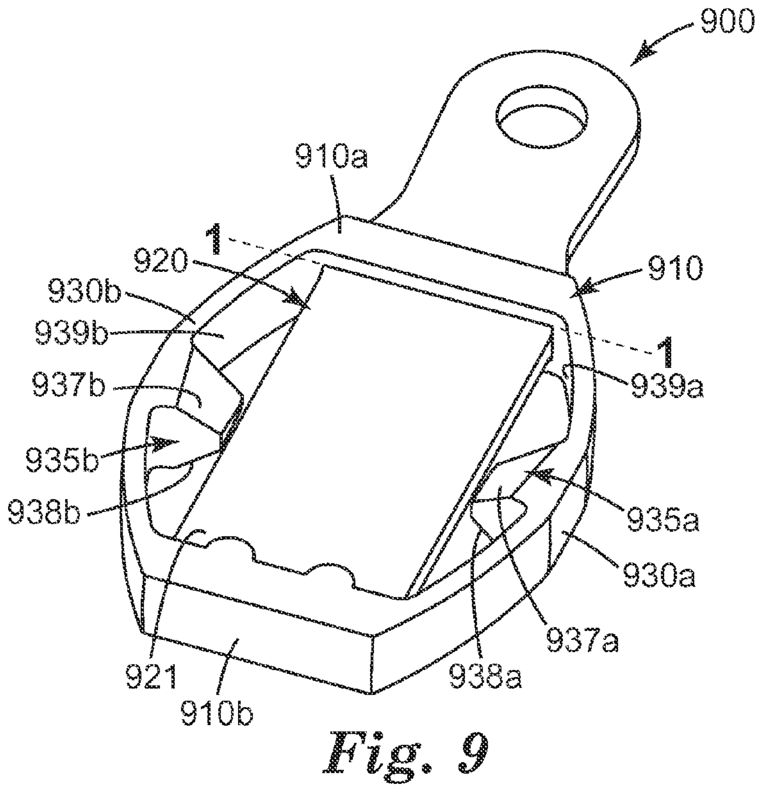
FIG. 9 shows a front perspective view of an exemplary strap retaining device according to the present disclosure.
Figure 10:
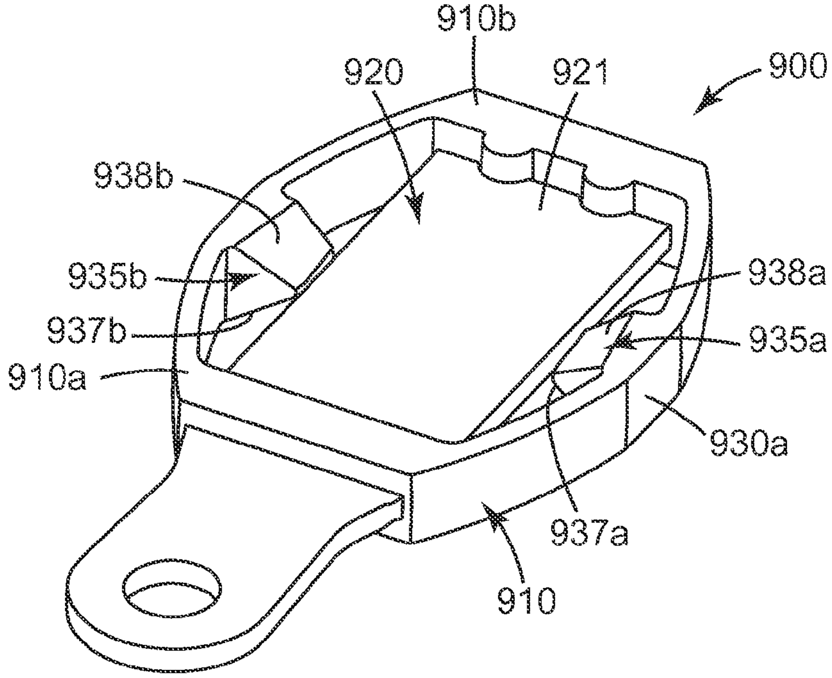
FIG. 10 shows a rear perspective view of an exemplary strap retaining device according to the present disclosure.
Figure 11:
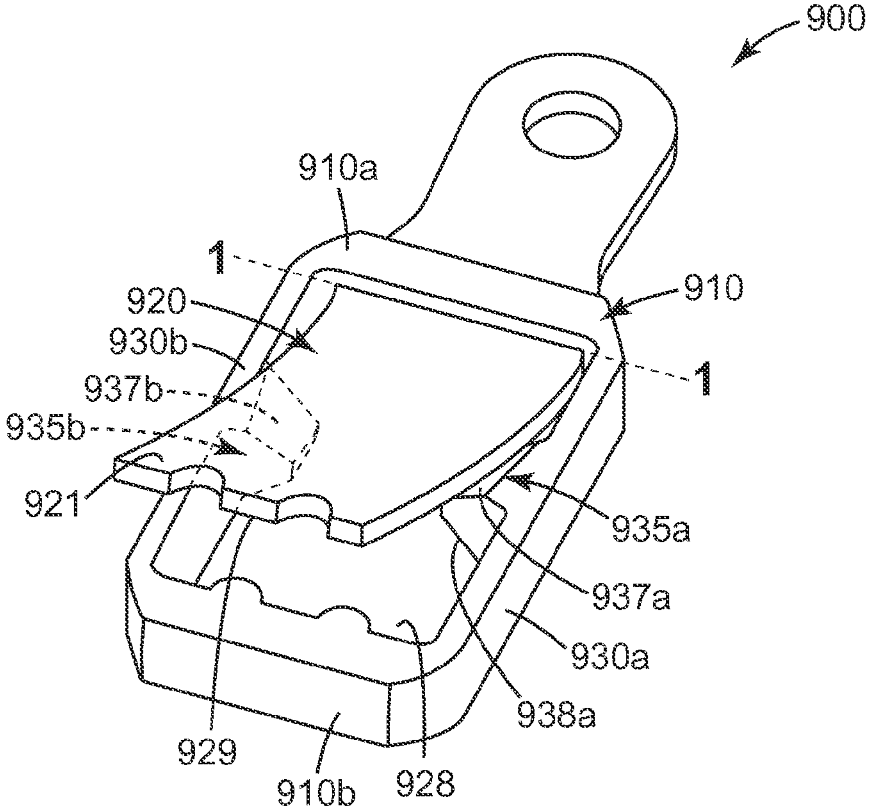
FIG. 11 shows a front perspective view of an exemplary strap retaining device according to the present disclosure in an activated position.

FIGS. 9, 10 and 11 show an exemplary embodiment of a strap retaining device 900 according to the present disclosure that is reversible such that strap retaining device 900 may be used in a first orientation or a second orientation. FIGS. 9 and 10 show front and rear views of strap retaining device 900, respectively, and FIG. 11 shows strap retaining device 900 in an activated position.

Strap retaining device 900 includes frame 910, retaining tab 920, and one or more actuation arms, such as actuation arms 930*a*, 930*b*. Frame 910 includes a first frame portion 910*a* and a second frame portion 910*b* joined by first and second actuation arms 930*a* and 930*b*. Actuation arms 930*a*, 930*b* exhibit a curved configuration and generally curve outward between first and second frame portions 910*a* and 910*b*.

Similar to strap retaining device 200 described above, retaining tab 920 may be pivotally connected to frame portion 910*a*, in an exemplary embodiment, such that retaining tab 920 may pivot or rotate relative to an axis, such as axis 1-1, for example. In a neutral position, retaining tab 920 and/or clamp portion 921, may apply a force against a strap positioned through strap channel 928.

In an exemplary embodiment, first and second actuation arms 930*a*, 930*b* are connected to frame 910, extending between first and second frame portions 910*a* and 910*b*, and having ends connected to frame portions 910*a* and 910*b*, respectively. Application of force along a length of arms 930*a*, 930*b*, such as a user squeezing arms 930*a*, 930*b* generally inwardly towards retaining tab 920, causes arms 930*a*, 930*b* to flex and/or straighten. Arms 930*a*, 930*b* are biased towards a curved neutral position, such as the position shown in FIG. 9, such that arms 930*a*, 930*b* return to the curved neutral position when a force from a user is removed.

Actuation arms 930*a*, 930*b* include actuation tabs 935*a*, 935*b* having actuation elements such as actuation ramps. Actuation ramps are configured to contact a surface of retaining tab 920 when arms 930*a*, 930*b* are flexed and/or straightened towards retaining tab 920. In an exemplary embodiment, actuation tabs 935*a*, 935*b* extend from an inner surface 939*a*, 939*b* of actuation arms 930*a*, and 930*b*. Actuation elements may include front ramps 937*a*, and 937*b* and rear ramps 938*a*, 938*b*, on front and rear sides respectively, of strap retaining device 900. In an exemplary embodiment, actuation arms and actuation elements are symmetrical when viewed from the front and the rear. Accordingly, a strap may be threaded through a strap channel 928 from the front to the rear or from the rear to the front, and a user need not consider the orientation of strap retaining device 900 when attaching a strap.

In a neutral position shown in FIG. 9, retaining tab 920 and/or retaining features 929 (FIG. 11) contact a strap (not shown) and may apply a force against the strap towards frame 910. A force applied to the strap may clamp the strap against frame 910 limiting movement of the strap through strap channel 928. The strap may be easily loosened by a user pushing actuating arms inwardly towards an actuated position shown in FIG. 11, for example. A first actuation element, such as front and rear ramps 937*a*, 937*b*, 938*a*, or 938*b*, is movable in a first plane from a neutral position to an actuated position in which front ramps 937*a* and/or 937*b* cause the retention tab to move in a second plane in a direction outwardly from front ramps 937*a* and/or 937*b*. The first actuation element, such as front and rear ramps 937*a*, 937*b*, 938*a*, or 938*b*, is further moveable in a first plane from a neutral position to an actuated position in which rear ramp 938*a* and/or 938*b* causes the retention tab to move in a second plane in a direction outwardly from rear ramp 938*a* and/or 938*b*. That is, retention tab 920 may pivot outwardly in the front direction or the rear direction depending on whether one or more front ramps 937*a*, 937*b* contact retention tab 920 or one or more rear ramps 938*a*, 938*b* contact retention tab 920. When a user squeezes actuation arms 930*a*, 930*b*, actuation arms 930*a*, 930*b* flex and/or straighten causing front ramps 937*a*, 937*b* to move in a first plane to contact engaging surfaces of retaining tab 920 and cause retaining tab 920 to move in a second plane in a direction outwardly from front ramps 937*a*, 937*b*. Alternatively, when a user squeezes actuation arms 930*a*, 930*b*, actuation arms 930*a*, 930*b* flex and/or straighten causing actuation rear ramps 938*a*, 938*b* to move in a first plane to contact engaging surfaces of retaining tab 920 and cause retaining tab 920 to move in a second plane in a direction outwardly from rear ramps 938*a*, 938*b*. Movement of retaining tab 920, and forward movement of a portion of frame 910 resulting from straightening of actuation arms 930*a*, 930*b*, increases a space between retaining tab 920 and a portion of frame 910 such that the strap may more easily pass through strap channel 928. With front ramps 937*a*, 937*b* or rear ramps 938*a*, 938*b* in an actuated position and retaining tab 920 raised, a user may easily increase a length of the strap.

A strap retaining device according to the present disclosure provides several advantages. A strap retaining device in which movement of actuation ramps in a first plane cause a retaining tab to move in second plane allows strap adjustments to be made by simply squeezing or pressing one or more actuation arms. Such a configuration facilitates one handed operation, or operation by a user wearing gloves that may limit dexterity. Although a retaining tab, such as retaining tab 220 for example, could be manipulated directly by a user, such operation may be difficult using only a single hand or a gloved hand, and may limit the ability of a user to quickly and easily lengthen a tensioning portion, for example, of a strap. Further, while prior devices may allow a strap to be shortened or tensioned by simply pulling the strap, a strap retaining device according to the present disclosure allows a strap to be easily lengthened or loosened, as well.

The foregoing detailed description and examples have been given for clarity of understanding only. No unnecessary limitations are to be understood there from. It will be apparent to those skilled in the art that many changes can be made in the embodiments described without departing from the scope of the disclosure. Any feature or characteristic described with respect to any of the above embodiments can be incorporated individually or in combination with any other feature or characteristic, and are presented in the above order and combinations for clarity only. Thus, the scope of the present disclosure should not be limited to the exact details and structures described herein, but rather by the structures described by the language of the claims, and the equivalents of those structures.

What is claimed is:

1. A strap retaining device for a personal protection device, comprising:

a frame comprising a first frame portion and a second frame portion;

a retention tab having a first end pivotally connected to the frame at the first frame portion and a second end portion not connected to the frame;

a strap channel between the second end of the retention tab and the second frame portion; and a first actuation arm connected to the frame and comprising a first actuation element movable towards the retention tab; and a strap positioned in the strap channel and looped about the second frame portion;

wherein the first actuation element is movable in a first plane from a neutral position to an actuated position in which the first actuation element causes the retention tab to move in a second plane that is substantially perpendicular to the first plane; and wherein the strap retention tab clamps the strap against the second portion of the frame in the neutral position.

2. The strap retaining device of claim 1, wherein the first actuation element is a ramp.

3. The strap retaining device of claim 1, wherein first actuation element contacts an angled surface of the retention tab in the actuated position.

4. The strap retaining device of claim 1, wherein the frame, strap retention tab, and actuation arm are integrally formed.

5. The strap retaining device of claim 1, wherein the frame, strap retention tab, and actuation arm are a unitary component.

6. The strap retaining device of claim 1, wherein the first actuation arm is a cantilever biased out of contact with the retention tab when in a neutral position.

7. The strap retaining device of claim 1, wherein the first actuation arm is curved when in a neutral position.

8. The strap retaining device of claim 1, further comprising a second actuation arm attached to the frame and comprising a second actuation element movable towards the retention tab.

9. The strap retaining device of claim 8, wherein the first actuation arm is positioned opposite the second actuation arm and the first and second actuation elements are movable towards each other.

10. The strap retaining device of claim 1, wherein the strap retaining device is made of plastic.

11. The strap retaining device of claim 1, wherein deflection of the actuation arm in the first plane towards the retention tab causes the retention tab to move in a second plane and reduce a force applied to the strap.

12. The strap retaining device of claim 1, further comprising an attachment element extending from the frame.

13. The strap retaining device of claim 12, wherein the attachment element extends away from the frame in a direction away from the retention tab.

14. The strap retaining device of claim 12, wherein the attachment element comprises a tab.

15. The strap retaining device of claim 12, wherein the attachment element comprises a hook.

16. The strap retaining device of claim 12, wherein the attachment element comprises a loop.

17. The strap retaining device of claim 1, wherein the first actuation arms and first actuation element are symmetrical when viewed from the front and the rear.

18. The strap retaining device of claim 1, wherein the first actuation element includes a front ramp and a rear ramp.

19. The strap retaining device of claim 18, wherein the first actuation element is movable in a first plane from a neutral position to an actuated position in which a front ramp causes the retention tab to move in a second plane in a direction outwardly from the front ramp, and the first actuation is further moveable in a first plane from a neutral position to an actuated position in which the rear ramp causes the retention tab to move in a second plane in a direction outwardly from the rear ramp.

20. A harness assembly for a respirator, comprising:

First and second strap retaining devices each including a frame comprising a first frame portion and a second frame portion, a retention tab having a first end pivotally connected to the frame at the first frame portion and a second end portion not connected to the frame, a strap channel and a first actuation arm connected to the frame and comprising a first actuation ramp movable in a first plane from a neutral position to an actuated position in which the first actuation ramp contacts a surface of the retention tab and causes the retention tab to move in a second plane that is perpendicular to the first plane;

a first strap positioned in a strap channel of the first strap retainer about a portion of the frame of the first strap retainer; and a second strap positioned in a strap channel of the second strap retainer about a portion of the frame of the second strap retaining devices;

wherein the first strap retaining device comprises a first attachment element and the second strap retaining device comprises a second attachment element and the first attachment element is attachable to the second attachment element, and wherein the strap retention tabs of the first and second strap retaining devices clamp the first and second straps, respectively, against the second portion of the frame when in a neutral position.

21. The harness assembly of claim 20, wherein the first and second straps are positionable about the neck of a wearer when the first attachment element is attached to the second attachment element.

22. The harness assembly of claim 20, wherein the first attachment element comprises a hook.

23. The harness assembly of claim 21, wherein the second attachment element comprises a loop.

24. The harness assembly of claim 20, further comprising:

a strap support positionable about a user's head and including a strap retainer receiver;

a third strap retaining device including a frame, a retention tab pivotally connected to the frame, a strap channel and a first actuation arm connected to the frame and comprising a first actuation ramp movable in a first plane from a neutral position to an actuated position in which the first actuation ramp contacts a surface of the retention tab and causes the retention tab to move in a second plane that is perpendicular to the first plane; and a third strap positioned in a strap channel about a portion of the frame of the third strap retaining device;

wherein the strap retainer comprises a third attachment element attachable to the strap retainer receptacle.

25. The harness assembly of claim 24, wherein the third attachment element comprises an anchoring tab.

26. The harness assembly of claim 24, wherein the third strap is positionable about the head of a user when the third attachment element is attached to the strap retainer receptacle of the strap support.

* * * * *